United States Patent [19]
Lewis et al.

[11] Patent Number: 5,436,345
[45] Date of Patent: Jul. 25, 1995

[54] METHOD FOR MAKING A 4-HYDROXY-TETRAORGANOPIPERIDINYLOXY

[75] Inventors: Larry N. Lewis, Scotia; James E. Pickett, Schenectady, both of N.Y.

[73] Assignee: General Electric Company, Schenectady, N.Y.

[21] Appl. No.: 304,297

[22] Filed: Sep. 12, 1994

[51] Int. Cl.$^6$ .......................................... C07D 211/72
[52] U.S. Cl. ................................................... 546/290
[58] Field of Search .......................................... 546/290

[56] References Cited

U.S. PATENT DOCUMENTS

| | | | |
|---|---|---|---|
| 3,258,477 | 6/1966 | Plueddemann et al. | 556/440 |
| 4,021,310 | 5/1977 | Shimizu et al. | 203/8 |
| 4,385,153 | 5/1983 | Ritter | 524/522 |
| 4,709,067 | 11/1987 | Chu et al. | 556/440 |

OTHER PUBLICATIONS

CA 120: 244682, (Galbo, EP 569334 Nov. 10, 1993).
E. G. Janzen, Spin Trapping, Chem. Eng. News 43, 50 (Sep. 27, 1965), Amer. Chem. Soc. (pp. 31–40).
I. H. Leaver et al., E.S.R. of Nitroxide Radicals, Aust. J. Chem. 1969, (pp. 1891–1900).
J. C. Bevington and N. A. Ghanem, The Mechanisms of Inhibition and Retardation in Radical Polymerizations, Part III, The Use of a Stable Free Radical as an Inhibitor, J. of Polymer Science, 1956, (pp. 3506, 3507 and 3509).
R. C. Lamb et al., Organic Peroxides, III. The Behavior of Cyclohexaneformyl Peroxide in the presence of Excess Stable Radicals. The Simultaneous Determination of Kinetics and Free Radical Efficiencies in the Thermal Decompositions of Free Radical Initiators, J. Phys. Chem. 1963, pp. 914–917).
C. Anderson Evans, Spin Trapping, Aldrichimica Acta. vol. 12, No. 2, 1979 (pp. 23, 25, 26–29).
P. D. Bartlett, Galvinoxyl (2,6-Di-tert-butyl-a-(3-,5-di-tert-butyl-4-oxo-2,5-cyclohexadiene-1-ylidene)-p-tolyloxy) As a Scavenger of Shorter-lived Free Radicals, J. Chem. Soc. 1962 (99.2596–2601).
J. F. Areizaga et al., Galvinoxyl As Scavenger in the Radical Polymerization of Styrene Initiated by AIBN, Makromol. Chem. Macromol. Symp. 20/21, 1988 (pp. 77, 79–82).
S. F. Nelsen, Azocumene. I. Preparation and Decomposition of Azocumene. Unsymmetrical Coupling Products of the Cumyl Radical, J. Am. Chem. Soc., 1965, (pp. 137–142).
L. N. Lewis et al., Ultraviolet-Curable, Abrasion-Resistant, and Weatherable Coatings with Improved Adhesion, J. of Applied Polymer Science, vol. 42, 1991, (pp. 1551–1556).
M. Stickler, Experimental Techniques in Free Radical Polymerization Kinetics, Makromol Chem. Macromol. Symp. Oct. 11, 1987, (pp. 17–69).

*Primary Examiner*—Johann Richter
*Assistant Examiner*—Catherine S. Kilby Scalzo
*Attorney, Agent, or Firm*—Ann G. Robinson; William H. Pittman

[57] ABSTRACT

A method is provided for making a 4-hydroxy-tetraorganopiperidinyloxy, such as 4-OH TEMPO. These free radical spin-traps can be used as anaerobic inhibitors which have been found useful for polymerizing reactive acrylic monomers.

8 Claims, No Drawings

METHOD FOR MAKING A 4-HYDROXY-TETRAORGANOPIPERIDINYLOXY

CROSS-REFERENCE TO RELATED APPLICATIONS

Reference is made to copending applications Ser. Nos. 08/304,300; 08/304,298; and 08/304,299, filed concurrently herewith and copending application Ser. No. 08/220,319, filed Mar. 30, 1994.

BACKGROUND OF THE INVENTION

The present invention relates to a method for making a 4-hydroxy-2,2,6,6-tetraorgano-1-piperidinyloxy, which can be employed as an anaerobic gelation inhibitor during the stripping step in the production of silicon containing polyacrylate hardcoat compositions.

As shown by Chung, U.S. Pat. No. 4,478,876, a process is provided for applying a UV curable silicon containing polyacrylate hardcoat composition onto a substrate, such as a thermoplastic substrate. The UV cure of the Chung polyacrylate hardcoat composition is effected in a non-inert atmosphere, such as air.

In the preparation of a UV curable silicon containing polyacrylate hardcoat composition, an aqueous colloidal silica is initially treated with an alkoxysilylacrylate such as methylacryloxypropyltrimethoxysilane. Water is then removed from the mixture in the form of an aqueous/organic solvent azeotrope. Prior to stripping, a polyfunctional reactive acrylic monomer, such as hexanedioldiacrylate, can be added to the mixture to provide an acrylic matrix for the silylated colloidal silica. Experience has shown that gelation of the silicon containing polyacrylate hardcoat mixture can occur readily during the distillation step, unless an inhibitor, such as methylhydroquinone (MEHQ) is used. As taught by Kurland, J. Poly. Sci. Poly Chem. Ed., 18 (1980) 1139, inhibitors such as MEHQ require oxygen to be effective. As a result, safety concerns have arisen concerning the distillation of large volumes of organic solvent at elevated temperatures in the presence of air or oxygen.

As shown in copending application RD-23,492 filed concurrently herewith, anaerobic gelation inhibitors have been found useful for making silicon containing polyacrylate hardcoats in a non-oxidizing atmosphere. Particularly useful anaerobic gelation inhibitors are the free radical derivatives of tetraorganopiperdinyloxy compounds such as 4-hydroxytetramethylpiperdinyloxy (4-OH TEMPO) having the formula,

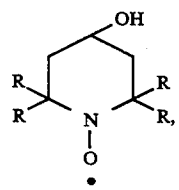
(1)

where R is a $C_{(1-8)}$ alkyl radical and preferably methyl.

However, due to the limited availability of source materials, for tetraorganopiperdinyloxy compounds, a satisfactory synthesis of 4-OH TEMPO has not been economically feasible.

It would be desirable therefore to be able to provide an economic procedure for synthesizing anaerobic gelation inhibitors, such as 4-OH TEMPO, to satisfy the need for replacing anaerobic inhibitors such as MEHQ during the production of silicon containing polyacrylate hardcoat compositions.

SUMMARY OF THE INVENTION

The present invention is based on the discovery that a tetraorganopiperidinol having the formula,

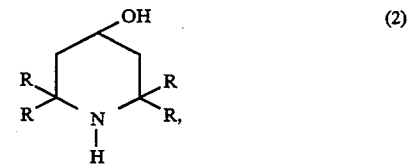
(2)

can be oxidized to a 4-hydroxy-tetraorganopiperidinyloxy, such as 4-hydroxy TEMPO of formula 1. It has been further found that the tetraorganopiperidinol of formula 2 can be synthesized from a bis(tetraorganopiperidinyl)ester of the formula:

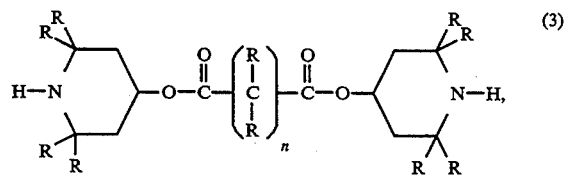
(3)

where R is as previously defined and n has a value of 2-8 inclusive. In addition it has discovered that a commercially available source material for a bis(tetraorganopiperidinyl) ester of formula (3) is the photo-stabilizer bis (2,2,6,6-tetramethyl-4-piperidinyl)sebacate, or Tinuvin ® 770 of the Ciba Geigy Co.

STATEMENT OF THE INVENTION

There is provided by the present invention, a method for making a 4-hydroxy-tetraorganopiperidinyloxy of formula (1), comprising, (A) heating a bis(tetraorganopiperidinyl)ester of formula (3) in the presence of a basic aqueous/organic solvent to produce a tetraorganopiperidinol of formula 2, (B) recovering the tetraorganopiperidinol of (A), and, (C) oxidizing the tetraorganopiperidinol of (B) to produce the corresponding 4-hydroxy-tetraorganopiperidinoxy.

Some of the bis (tetraorganopiperidinyl) esters included within formula 3 are compounds having the formulas,

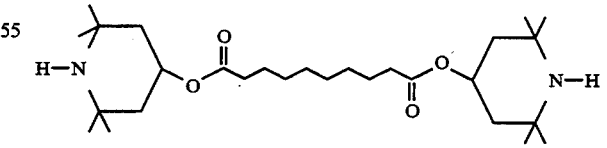

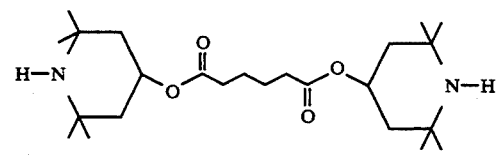

Oxidizing agents which can be used to convert tetraorganopiperdinol of formula 2 to 4-hydroxy-tetraorganopiperidinyloxy compounds are for example, m-chloroperoxy benzoic acid and tungsten catalyzed hydrogen peroxide.

In the practice of the invention, a bis(tetraorganopiperidinyl)ester, referred to hereinafter as the "bis-ester" is contacted with a basic aqueous/organic solvent solution. The mixture can be warmed at a temperature of about 25° C. to about 100° C. for a time sufficient to effect the saponification of the bis-ester and the formation of the corresponding diester salt and the tetraorganopiperidinol.

Suitable organic solvents which can be used are preferably alcohols for example ethanol, methanol, and 2-propanol.

Bases which can be used are alkali metal hydroxides, such as sodium hydroxide, potassium hydroxide and lithium hydroxide.

Recovery of the tetraorganopiperidinol can be facilitated by effecting the removal of the bisester salt from the hydroylsis mixture by filtration, centrifugation, or other standard means.

Oxidation of the tetraorganopiperidinol to the corresponding 4-hydroxy-tetraorganopiperidinyloxy can be effected at a temperature of about 25° C. to about 100° C.

The following example is given by way of illustration and not by way of limitation. All parts are by weight unless otherwise indicated.

EXAMPLE

A mixture of 250 g of bis (2,2,6,6-tetramethyl-4-piperidinyl)sebacate, (Tinuvin ® 770 of the Ciba Geigy Co), 2 L of ethanol, 42 g of sodium hydroxide, and 50 ml of water were heated at 70° C. for 15 hour. A white precipitate formed which was removed by filtration and then washed with 500 ml of ethanol. The combined filtrate was evaporated in vacuo to provide 172 g of an off white solid after the product was dried at 60° C. and 30 torr. Based on method of preparation and $^1$H NMR, the product was 2,2,6,6-tetramethyl-4-piperidinol.

A mixture of 6 g of 2,2,6,6-tetramethyl-4-piperidinol, 80 ml of water, 0.4 g of sodium tungstate, 0.4 g Na$_4$EDTA and 8 ml of a 30% solution of hydrogen peroxide was heated at 50° C. for 14 hours. Potassium carbonate was then added to the resulting red solution which was stirred. The aqueous solution was extracted with three 75 ml portions of ether. There was obtained, 4.7 g of an orange solid from the ether extracts after drying and stripping in vacuo. Based on method of preparation its IR spectrum, and 65°–67° C. melting point, the solid was tetramethylpiperdinyloxy (4-OH TEMPO).

A mixture of 86.9 g of Nalco 1034A of the Nalco chemical company (an aqueous colloidal silica dispersion having 34% of SiO$_2$), 200 ml of isopropyl alcohol, (IPA) 13 g of methylacryloxypropyltrimethoxysilane (MAPTMS) and 0.15 g of 4-OH TEMPO is heated and stirred at 60° C. for 2 hr with nitrogen bubbling through the mixture. There is then added to the mixture, 36.2 g of hexanedioldiacrylate (HDDA) and 371 ml of isopropyl alcohol and the mixture is vacuum stripped at <50 mm Hg with a nitrogen bleed. There is obtained 61 g of an oil having a viscosity of 55 cps. Based on method of preparation, the oil is a radiation curable acrylate containing silicone hardcoat composition.

Although the above example is directed to only a few of the many variables which can be used in the practice of the method of the present invention, a much broader variety of reactants and conditions are shown in the description preceding this example.

What is claimed is:

1. A method for making a 4-hydroxy-tetraorganopiperidinyloxy comprising,
   (A) heating a bis(tetraorganopiperidinyl)ester in the presence of a basic aqueous/organic solvent to produce a tetraorganopiperidinol
   (B) recovering the tetraorganopiperidinol of (A), and,
   (C) oxidizing the tetraorganopiperidinol of (B) to produce the 4-hydroxy-tetraorganopiperidinoxy.

2. A method in accordance with claim 1, where the bis(tetraorganopiperidinyl) ester is a bis (2,2,6,6-tetramethyl-4-piperidinyl) sebacate.

3. A method in accordance with claim 1, where the bis(tetraorganopiperidinyl)ester is a bis (tetramethyl-4-piperidinyl)adipate.

4. A method in accordance with claim 1, where an alkali metal tungstate and hydrogen peroxide is used as the oxidizing agent.

5. A method for making tetramethylpiperdinyloxy in accordance with claim 1.

6. A method in accordance with claim 1, where the organic solvent is ethanol.

7. A method for making a 4-hydroxy-tetraorganopiperidinol by heating a bis(tetraorganopiperidinyl)ester in the presence of a basic aqueous/organic solvent.

8. A method for making tetramethylpiperdinol in accordance with claim 7.

* * * * *

UNITED STATES PATENT AND TRADEMARK OFFICE
CERTIFICATE OF CORRECTION

PATENT NO.  : 5,436,345
DATED       : July 25, 1995
INVENTOR(S) : Larry N. Lewis, et al It is certified that error appears in the above-indentified patent and that said Letters Patent is hereby corrected as shown below:

On the title page, under Attorney, Agent, or Firm, the name "Ann G. Robinson" should be deleted.

Signed and Sealed this

Fourteenth Day of November, 1995

Attest:

BRUCE LEHMAN

*Attesting Officer*  *Commissioner of Patents and Trademarks*